United States Patent [19]

Alexander et al.

[11] Patent Number: 4,985,518

[45] Date of Patent: Jan. 15, 1991

[54] PROCESS FOR PREPARING WATER-ABSORBING RESINS

[75] Inventors: William Alexander, Naperville; Mark Anderson, Wheaton; Barbara R. Regan, Glenview, all of Ill.

[73] Assignee: American Colloid Company, Arlington Heights, Ill.

[21] Appl. No.: 389,616

[22] Filed: Aug. 4, 1989

Related U.S. Application Data

[63] Continuation of Ser. No. 85,974, Aug. 14, 1987, abandoned, which is a continuation-in-part of Ser. No. 730,638, May 6, 1985, Pat. No. 4,654,393, which is a continuation of Ser. No. 436,428, Oct. 25, 1982, Pat. No. 4,612,250, which is a continuation-in-part of Ser. No. 710,702, Mar. 11, 1985, Pat. No. 4,612,250, which is a continuation of Ser. No. 460,037, Jan. 21, 1983, Pat. No. 4,525,527, which is a continuation-in-part of Ser. No. 748,528, Jun. 25, 1985, abandoned, which is a continuation-in-part of Ser. No. 748,246, Jul. 24, 1985, abandoned, which is a continuation-in-part of Ser. No. 854,000, Mar. 21, 1986, Pat. No. 4,677,174, which is a continuation-in-part of Ser. No. 872,654, Jun. 10, 1986, Pat. No. 4,755,562.

[51] Int. Cl.$^5$ .............................................. C08F 30/04
[52] U.S. Cl. ...................................... 526/240; 526/555; 526/556; 526/812
[58] Field of Search ............... 526/240; 524/555, 556, 524/812

[56] References Cited

U.S. PATENT DOCUMENTS

| | | | |
|---|---|---|---|
| Re. 31,822 | 9/1978 | Erickson | 428/224 |
| 2,956,046 | 10/1960 | Glavis | 526/202 |
| 2,978,501 | 4/1961 | Adams | 562/598 |
| 2,980,655 | 4/1961 | Jones | 526/204 |
| 2,985,625 | 5/1961 | Glass | 526/261 |
| 2,985,631 | 5/1961 | Jones | 526/219.3 |
| 3,215,659 | 11/1965 | Spaulding | 524/512 |
| 3,426,004 | 2/1969 | Wagner | 526/274 |
| 3,670,731 | 6/1972 | Harmon | 604/368 |
| 3,723,413 | 3/1973 | Chatterjee | 536/87 |
| 3,784,597 | 1/1974 | Fujimoto | 525/366 |
| 3,901,236 | 8/1975 | Assarsson | 604/368 |
| 3,980,663 | 9/1976 | Gross | 524/389 |
| 3,997,484 | 12/1976 | Weaver | 525/54.32 |
| 4,057,521 | 11/1977 | Gross | 524/379 |
| 4,058,124 | 11/1977 | Yen | 604/368 |
| 4,062,817 | 12/1977 | Westerman | 525/330.2 |
| 4,076,663 | 2/1978 | Masuda | 525/54.31 |
| 4,124,748 | 11/1978 | Fujimoto | 525/60 |
| 4,190,562 | 2/1980 | Westerman | 526/238.23 |
| 4,200,736 | 4/1980 | Shinohara | 536/87 |
| 4,286,082 | 8/1981 | Tsubakimoto | 526/240 |
| 4,295,987 | 10/1981 | Parks | 252/194 |
| 4,340,706 | 7/1982 | Obayashi | 526/207 |
| 4,351,922 | 9/1982 | Yoshida | 525/116 |

(List continued on next page.)

FOREIGN PATENT DOCUMENTS 1160984  1/1984  Canada .......................... 204/91.64

*Primary Examiner*—Joseph L. Schofer
*Assistant Examiner*—Alex H. Walker
*Attorney, Agent, or Firm*—Marshall, O'Toole, Gerstein, Murray & Bicknell

[57] ABSTRACT

A method of preparing a solid water absorbing resin including mixing a monomer solution of (A) acrylic acid neutralized 70–100 mole percent; and (B) a water-miscible to water-soluble polyvinyl monomer in a combined concentration of at least 30 wt. %; with water to form a mixed monomer solution, and adding a thermal initiator and a redox initiator to the mixed monomer solution to form an initiated mixed monomer solution, and wherein the mixed monomer solution is at a temperature below the decomposition temperature of the thermal initiator when the thermal initiator is added to the mixed monomer solution and wherein the temperature of the mixed monomer solution is high enough such that addition of the redox initiator thereto causes sufficient polymerization of the monomers to raise the temperature of the initiated mixed monomer solution to a level sufficient that the thermal initiator decomposes sufficiently to provide, together with the redox initiator, substantially complete polymerization.

29 Claims, 1 Drawing Sheet

U.S. PATENT DOCUMENTS

| | | | |
|---|---|---|---|
| 4,389,513 | 6/1983 | Miyazaki | 525/186 |
| 4,415,388 | 11/1983 | Korpmann | 156/78 |
| 4,473,689 | 9/1984 | Login | 526/81 |
| 4,500,670 | 2/1985 | McKinley | 524/445 |
| 4,522,997 | 6/1985 | Schmitz | 522/167 |
| 4,525,527 | 6/1985 | Takeda | 524/831 |
| 4,535,098 | 8/1985 | Evani | 521/149 |
| 4,552,938 | 11/1985 | Mikita | 526/240 |
| 4,562,114 | 12/1985 | Sawanishi | 428/372 |
| 4,612,250 | 9/1986 | Takeda | 428/500 |
| 4,618,631 | 10/1986 | Takeda | 521/109.1 |
| 4,654,039 | 3/1987 | Brandt | 604/368 |
| 4,654,393 | 3/1987 | Mikita | 526/240 |
| 4,677,174 | 6/1987 | Alexander | 526/240 |

PROCESS FOR PREPARING WATER-ABSORBING RESINS

CROSS REFERENCE TO RELATED APPLICATIONS

This is a continuation of application Ser. No. 85,974, filed Aug. 14, 1987 which is a continuation-in-part of copending application Ser. No. 730,638 filed May 6, 1985, now U.S. Pat. No. 4,654,393 which is a continuation of application Ser. No. 436,428 filed Oct. 25, 1982, now U.S. Pat. No. 4,552,938; and a continuation-in-part of application Ser. No. 710,702 filed Mar. 11, 1985 now U.S. Pat. No. 4,612,250 which is a continuation of application Ser. No. 460,037 filed Jan. 21, 1983, now U.S. Pat. No. 4,525,527; and a continuation-in-part of application Ser. No. 748,528 filed Jun. 25, 1985, now abandoned; and a continuation-in-part of application Ser. No. 748,246 filed Jul. 24, 1985 now abandoned; and a continuation-in-part of Ser. No. 854,000 filed Mar. 21, 1986 now U.S. Pat. No. 4,677,174; and a continuation-in-part of Ser. No. 872,654 filed Jun. 10, 1986, now U.S. Pat. No. 4,755,562.

FIELD OF THE INVENTION

The present invention relates to a method and apparatus for manufacturing polyacrylate resins having improved water absorbing properties and more particularly to an improved process and apparatus for preparing, either batch-wise, or continuously, cross-linked polymers of acrylic acid and a polyvinyl monomer having a new and unexpectedly low free acrylic monomer level. "Free monomer" or "free acrylic monomer", as used herein, includes any free acrylic acid in monomer form, as well as any acrylic monomer in the neutralized or salt form, which has not reacted to form a polymer.

BACKGROUND OF THE INVENTION AND PRIOR ART

Water absorbing resins have found wide use in sanitary goods, hygenic goods, water retaining agents, dehydrating agents, sludge coagulants, thickening agents, condensation preventing agents and release control agents for various chemicals. Water absorbing resins heretofore known include hydrolysis products of starch-acrylonitrile graft polymers, carboxymethylcellulose, cross-linked polyacrylate products and other resins such as polyvinyl alcohol, polyethylene oxide and polyacrylonitrile resins. Of these water absorbing resins, the hydrolysis products of starch and acrylonitrile graft polymers have comparatively high ability to absorb water but require a cumbersome process for production and have the drawbacks of low heat resistance and decaying or decomposing easily due to the presence of starch.

One of the processes for polymerizing acrylic acid and acrylates is aqueous solution polymerization. The polymer obtained by this process is soluble in water and, therefore, is cross-linked to modify the polymer into a useful water absorbing resin. However, even if the modification is effected by reacting a cross-linking agent concurrently with or after aqueous solution polymerization, the resulting reaction product is in the form of a highly viscous aqueous solution or a gel containing absorbed water which is difficult to handle. Thus, the aqueous solution or gel must be dehydrated (dried) to obtain a water absorbing resin in the desired solid or powder form. It is nevertheless difficult to dry the reaction product efficiently by the usual rotary drum roller method or spray drying method because care must be taken to avoid excessive cross-linking which results from overheating during drying, and insufficient drying results in reduced cross-linking density. Extreme difficulties are therefore encountered in preparing a product of a desired low water content and good water absorbing ability.

SUMMARY OF THE INVENTION

An object of the present invention is to provide a process and apparatus for preparing, either batch-wise, or continuously, a water absorbing cross-linked acrylate resin of low water content and low free monomer content by aqueous solution polymerization.

Another object of the present invention is to provide a process and apparatus for preparing, either batch-wise, or continuously, a water absorbing cross-linked acrylate resin of low water content and low free monomer content by aqueous solution polymerization without any additional dehydrating or drying step.

Another object of the present invention is to provide a process and apparatus for preparing, either batch-wise or continuously, a cross-linked polyacrylate resin by polymerization of acrylic acid neutralized 70-100 mole percent, and a water-miscible or water soluble polyvinyl monomer in a combined concentration of 30 to 80 wt. % in water and initiating polymerization without external heating.

Another object of the present invention is to provide a process and apparatus for preparing, either batch-wise or continuously, a cross-linked polyacrylate resin by co-polymerization of acrylic acid neutralized 70-100 mole percent, with acrylamide and a polyvinyl monomer in proportions of 0 to 30 mole percent acrylamide and 70-100 combined mole percent of neutralized acrylic acid and free acrylic acid.

Another object of the present invention is to provide a batch or continous process and apparatus for producing a polyacrylate resin cross-linked with 0.2 weight percent to 0.6 weight percent based on the weight of monomers, of a water miscible or water soluble polyvinyl monomer cross-linking agent to achieve a "dry feel" to the resin after significant water absorption.

Still another object of the present invention is to provide a batch or continuous process and apparatus for producing a water absorbing polyacrylate resin wherein a combination of neutralizing agents are used to neutralize acrylic acid 70-100 mole percent, wherein one or more neutralizing agents reacts exothermically with acrylic acid and one or more neutralizing agents reacts endothermically with acrylic acid to avoid overheating of the monomer reactants.

Another object of the present invention is to provide a new and improved process and apparatus for producing a water absorbing polyacrylate resin by polymerizing acrylic acid substantially completely with a combination of a thermal initiator and a chemically distinct redox initiator, leaving unexpectedly low non-polymerized acrylic acid, or free monomer levels, after polymerization, by using a combination of initiators.

In brief, the present invention is directed to a process and apparatus for preparing, either batchwise or continuously, water absorbing, cross-linked acrylate resins by aqueous polymerization of (A) acrylic acid neutralized 70 to 100 mole percent for example with ammonia, and/or caustic alkali and/or an amine; with (B) acrylamide in a mole ratio of 70 to 100 mole percent (A) to 30:0 mole percent (B); and (C) a water miscible or a water soluble polyvinyl monomer in an amount of 0.001 to 0.3 weight percent based on the total weight of (A) and (B). To achieve a low free monomer (acrylic acid or neutralized acrylic acid) level in the product, a combination of a thermal initiator and a redox initiator is used to achieve free monomer levels less than 1000 PPM, and particularly free monomer levels less than 500 PPM, directly after polymerization, without further treatment. To achieve the full advantage of the present invention the monomer concentration is at least 50 wt. % of the aqueous solution. A "dry feel" is obtained at a polyvinyl monomer concentration of at least 0.2 wt. percent based on the weight of monomer in the aqueous solution.

In accordance with the present invention, a heated aqueous solution comprising (A) acrylic acid neutralized 70 to 100 mole percent for example with ammonia, and/or caustic alkali and/or an amine; and (B) a water-miscible to water-soluble polyvinyl monomer, water and, when desired, an organic solvent having a boiling point of 40 to 150° C., and having a combined monomer concentration of (A) plus (B) of 30 to 80 wt. % is subjected to polymerization, either batch-wise, or continuously, in the presence of a combination of polymerization initiators without external heating while allowing water to evaporate off.

DETAILED DESCRIPTION OF THE INVENTION

In accordance with the present invention a crosslinked polyacrylate resin is prepared by aqueous solution polymerization while dehydrating or drying the reaction product during polymerization by utilizing the exothermic heat from the polymerization and crosslinking reactions for drying.

It has been found that acrylic acid neutralized in the range of 70 to 100 mole percent will polymerize and cross-link rapidly with a polyvinyl monomer cross-linking agent to drive away excess water leaving a solid water absorbing resin having a desired degree of polymerization as well as new and unexpectedly low free monomer levels and water absorbing capacity. A combination of thermal and redox polymerization initiators is added to the aqueous monomer mixture to aid in polymerization and to reduce the free monomer content to unexpectedly low levels.

According to the present invention, a hot aqueous mixed monomer solution is prepared first comprising acrylic acid neutralized 70 to 100 mole percent, a water-miscible or water-soluble polyvinyl monomer, and water wherein the mixed monomer solution contains the acrylate monomer and the polyvinyl monomer in a combined concentration of 30 to 80 wt. %. To achieve the full advantage of the present invention, the acrylic acid, acrylate and polyvinyl monomers are present in the mixed monomer solution in a combined concentration of less than 70 weight percent of the monomer solution. In accordance with another important embodiment of the present invention, the combined concentration of the acrylic acid, acrylate and polyvinyl monomers is less than 55 weight percent of the monomer solution. The concentration of the monomers is deliberately determined considering the state of the solution (i.e. as to whether or not the monomers can be completely dissolved in water), ease of the reaction of the monomers, and escape of the monomers due to scattering during the reaction. The aqueous solution can be prepared easily usually by placing acrylic acid, a strong alkali such as potassium hydroxide and/or ammonium hydroxide or a basic amine for neutralizing the acid, and the polyvinyl monomer into water in such amounts that the resulting solution has the above-mentioned 30–80 wt. % monomer concentration. To dissolve the monomers thoroughly, the mixture can be heated to an elevated temperature. Any strongly basic alkali metal compound can be used for neutralization of the acrylic acid, such as potassium hydroxide, sodium hydroxide, lithium hydroxide, cesium hydroxide, potassium carbonate or sodium carbonate. Although it is desirable to use the neutralizing agent usually in an amount sufficient to neutralize acrylic acid 100 mole %, there is no particular need to neutralize the acid 100% insofar as the neutralizing agent, e.g., hydroxide, is used in such an amount as to achieve not less than about 70% neutralization. Accordingly, the aqueous solution may contain up to about 30% of free acrylic acid. However, a large quantity of free acrylic acid, if present in the aqueous solution, is likely to partly splash out of the system to result in a loss during the reaction, leading to a reduced degree of polymerization. Use of an excessive amount of the neutralizing agent will not raise any particular problem, but the excess does not participate in the polymerization reaction and is therefore useless.

In accordance with another important feature of the present invention, a combination of neutralizing agents, one which reacts endothermically with acrylic acid, e.g., a basic ammonium compound such as ammonium carbonate and/or ammonium hydroxide, and one which reacts exothermically with acrylic acid, e.g., potassium hydroxide, are used to maintain the monomer reactants in the mixed monomer solution at a proper temperature below the decomposition temperature of a thermal initiator without the necessity of cooling the reaction vessel.

In accordance with the present invention, acrylic acid neutralized 70–100 mole percent is mixed with a water-miscible or water-soluble polyvinyl monomer in an aqueous solution at a temperature of about 85° F. to about 150° F., generally about 90° F. to about 125° F., and particularly 90–110° F., and continuously fed to a polymerization reaction station.

The temperature of the mixed monomer solution can vary considerably in accordance with the process of the present invention prior to the addition of the thermal and redox initiators, depending upon the particular thermal initiator added. In any event, the initial temperature of the mixed monomer solution should be below the temperature at which the thermal initiator decomposes or otherwise causes substantial polymerization initiation and the temperature of the mixed monomer solution should be high enough that the redox initiator causes sufficient polymerization at the initial temperature of the mixed monomer solution to raise the temperature of the mixed monomer solution to a level sufficient that the thermal initiator, together with the redox initiator, causes substantially complete polymerization leaving less than about 1000 PPM free monomer, and generally less than about 500 PPM free monomer. Free monomer levels less than 200 PPM and even less than

Figure 1:
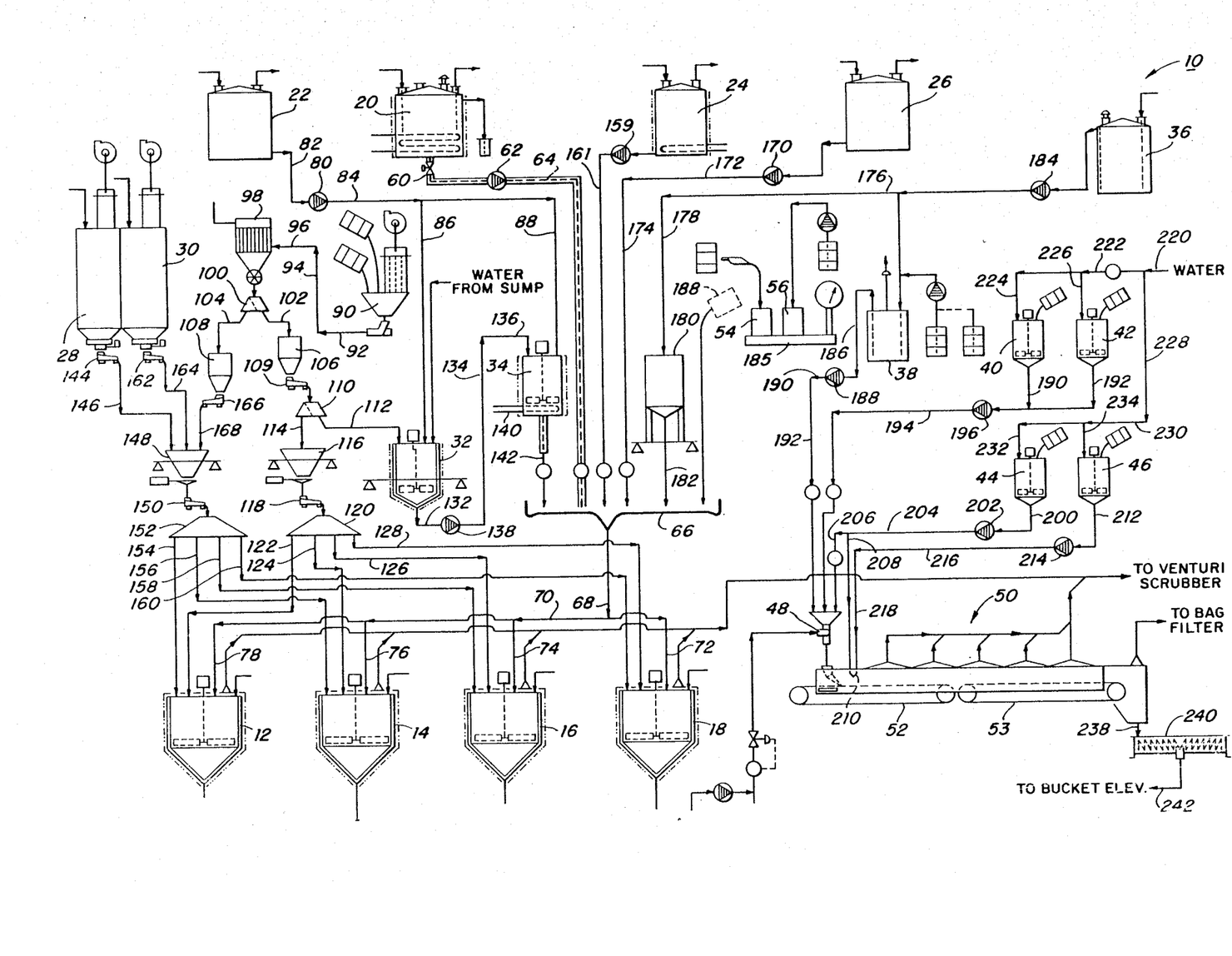
FIG. 1 is a schematic view of the continuous process and apparatus of the present invention.

100 PPM have been achieved in accordance with the process of the present invention. The combination of initiators can be added to the mixed monomer solution in a batch process, or continuously as shown in the drawing.

In accordance with the continuous process shown in the drawing, the mixed monomer solution is subjected to a polymerization reaction and a cross-linking reaction by the continuous addition of a combination of polymerization initiators in an in-line mixing device just prior to depositing the initiated mixed monomer solution onto an endless moving conveyor belt. The polymerization reaction begins within a very short period of time, e.g., about 30 seconds, as a result of the redox initiator. Once the polymerization reaction begins, the exothermic heat of reaction raises the temperature of the mixed monomer solution to a degree that the thermal initiator also initiates further polymerization to substantial completion. If the monomer concentration is at least 30 percent by weight of the aqueous monomer mixture, the heat of the polymerization and cross-linking reactions will evaporate water rapidly from the reaction product as it travels down the endless belt to form a dry solid (less than 15 percent by weight water) water absorbing resin without the need for any subsequent drying step. The solid can be easily pulverized into a powder suitable for any desired use.

According to the continuous process embodiment of the invention, a hot, i.e. at least 85° F., aqueous solution is prepared first including acrylic acid neutralized 70 to 100 mole percent, optionally acrylamide, a water-miscible or water-soluble polyvinyl monomer, and water in one or more mixed monomer solution storage vessels. A thermal initiator and a redox initiator are stored in separate initiator storage vessels so that the reactants from the mixed monomer vessel and each of two initiator vessels are fed simultaneously into an in-line mixing device disposed in close proximity to a traveling endless conveyor belt. The aqueous solution can be prepared easily by placing (A) acrylic acid, and an amine, and/or a caustic alkali and/or ammonia for neutralizing the acid; (B) acrylamide (0–30 mole percent); and (C) a polyvinyl monomer into water to form a mixed monomer solution. To dissolve the monomers thoroughly, the mixture can be heated to an elevated temperature up to about 150° F., preferably below 125° F., especially 90–110° F.

The polyvinyl monomer to be used in both embodiments of the invention should be miscible with or soluble in water so that the monomer will be uniformly dissolved or dispersed in the aqueous solution of the monomer mixture. Examples of such polyvinyl monomers include bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

FORMULA (I)

wherein X is ethylene, propylene, trimethylene, hexamethylene, 2-hydroxypropylene, $(CH_2CH_2O)_nCH_2CH_2$—or , n and m are each an integer of from 5 to 40, and k is 1 or 2.

The compounds of the formula (I) are prepared by reacting polyols, such as ethylene glycol propylene glycol, trimethylolpropane, 1,6-hexanediol, glycerin, pentaerythritol, polyethylene glycol and polypropylene glycol, with acrylic acid or methacrylic acid.

FORMULA (II):

wherein λ is 2 or 3.

The compounds of the formula (II) are obtained by reacting polyalkylenepolyamines, such as diethylenetriamine and triethylenetetramine, with acrylic acid.

The polyvinyl monomer is used in an amount of about 0.001 to 0.6 wt. % of the amount of acrylic monomers in the aqueous monomer mixture. In accordance with an important embodiment of the present invention, the polyvinyl monomer should be present in the aqueous solution in an amount of at least 0.2 wt. % based on the total weight of monomers to provide a resin sufficiently cross-linked to have a "dry feel" after significant water absorption. If the polyvinyl monomer is included in the aqueous solution in an amount of 0.2 to 0.6 weight percent based on the weight of neutralized acrylic acid and polyvinyl monomers, the resulting polymer will have an exceedingly "dry feel" after significant absorption of water.

The aqueous mixed monomer solution is maintained at a desired temperature, depending upon the temperature at which the thermal initiator decomposes or otherwise becomes effective, and the degree to which the exothermic heat of reaction causes the temperature of the mixed monomer solution to rise as a result of the initiation by the redox initiator. The temperature of the mixed monomer solution should be high enough that the redox initiator causes the mixed monomer solution to rise in temperature to a degree that the thermal initiator decomposes or otherwise effectively continues the polymerization reaction. The temperature of the mixed monomer solution is usually maintained at about 100° F. to about 145° F., in accordance with the preferred thermal initiators disclosed hereinafter, preferably about 115° F. to about 125° F.

In accordance with an important feature of the present invention, it has been found that a combination of at least one thermal initiator with at least one redox initiator enables efficient polymerization while limiting the free monomer (acrylic acid and acrylic acid salt) content to less than 1000 PPM, and generally less than 500 PPM in the completed waterabsorbing polymer. Examples of useful redox initiators include a reducing agent, such as a sulfite or bisulfite of an alkali metal, such as ammonium sulfite, ammonium bisulfite, or ammonium metabisulfite; a persulfate of an alkali metal or ammonium persulfate; t-butyl butyl hydroperoxide; di-t-butyl hydroperoxide; t-butyl perbenzoate; t-butyl peroxy isopropyl carbonate; and peroxy-3,3,5 trimethylcyclohexane. These redox initiators can be used singly or in a suitable combination. Of these, especially preferable are a redox initiator including a combination of ammonium persulfate and sodium hydrogensulfite. These initiators are advantageously used usually in the form of an aqueous solution but can be dissolved in a suitable solvent, e.g., alcohol, if insoluble in water. The redox initiator is used in an amount, calculated as solids, of about 0.1 to about 10 %, preferably about 0.5 to about 5 %, of the combined weight of the monomers, namely acrylate (and free acrylic acid), acrylamide, and polyvinyl monomer. Depending on the amount and kind of the initiator, the initiator is usable together with isopropyl alcohol, alkylmercaptan or other chain transfer agents to control the molecular weight of the polyacrylate to be obtained.

Examples of suitable thermal initiators include azo initiators such as azobisisobutyronitrile; 4-t-butylazo-4'-cyanovaleric acid; 4,4'-azobis(4-cyanovaleric acid); 2,2'-azobis(2-amidinopropane)dihydrochloride; 2,2'-azobis(2,4-dimethylvaleronitrile); dimethyl 2,2'-azobisisobutyrate; 2,2'-azobis(2,4-dimethylvaleronitrile); (1-phenylethyl)azodiphenyl methane; 2,2'-azobis(2-methylbutyronitrile); 1,1'-azobis (1-cyclohexanecarbonitrile);2-(carbamoylazo)-isobutyronitrile; 2,2'-azobis(2,4,4-trimethylpentane); 2-phenylazo-2,4-dimethyl-4-methoxyvaleronitrile; 2,2'-azobis(2-methylpropane); 2,2'-azobis (N,N'-dimethyleneisobutyramidine)dihydrochloride; 2,2'-azobis(N,N'-dimethyleneisobutyramidine; 4,4'-azobis(4-cyanopentanoic acid); 2,2'-azobis (2-methyl-N-[1,1-bis(hydroxymethyl)-2-hydroxy-ethyl]propionamide); 2,2'-azobis[2-methyl-N-[1,1-bis(hydroxymethyl)ethyl]propionamide); 2,2'-azobis(2-methyl-N-(2-hydroxyethyl))-propionamide]; 2,2'-azobis(isobutyramide)dihydrate.

By the continuous addition of the combination of polymerization initiators, the mixed monomer solution is subjected to continuous polymerization at a polymerization station, such as on a surface of a liquid-impermeable conveyor belt or in a suitable reaction vessel, with evaporation of water without heating the system from outside. To achieve the full advantage of the present invention, the reaction is carried out by adding the combination of initiators, from separate initiator storage vessels, into the mixed monomer solution in a suitable in-line mixing device and causing the resulting initiated mixture to flow down onto and spread over a traveling conveyor belt. Alternatively, the initiators can be added to the mixed monomer solution as it is poured onto the conveyor belt.

The polymerization proceeds rapidly after admixing the initiators with the mixed monomer solution and is completed within a short period of time, usually in about 30 seconds to about 10 minutes. The reaction is exothermic, so that the reactants are rapidly heated from a reaction temperature of about 90° F. to about 125° F. to about 265° F. by the heat of polymerization. Consequently, particularly where the monomer concentration in the mixed solution is at least 50 percent by weight, the water evaporates from the system rapidly to give a relatively dry, solid polymer of low water content without resorting to any external heating or other further treatment. The water content of the polymer is usually up to about 15 %, and generally about 8 to 12 % by weight as recovered. Subsequently, the dry solid polymer can be made into the desired powder easily by a usual method, for example by pulverization, without a drying step.

In accordance with another important feature of the present invention, polystyrene and/or methylcellulose can be added to the mixed monomer solution in an amount of 0.5 to about 10 percent based on the total weight of monomers in the mixed monomer solution to increase the porosity and water absorbing capacity of the polymers. It has been found, quite surprisingly, that polystyrene and methylcellulose will substantially increase the water absorbing capacity of the resin described herein. To achieve the full advantage of the present invention, the polystyrene and methylcellulose should be added in an average grain size of less than or equal to 5 micrometers.

The water-absorbing polymer powder thus obtained has outstanding water absorbing ability, an unexpectedly low free monomer level, is useful for sanitary goods, paper diapers, disposable diapers and like hygenic goods, agricultural or horticultural water retaining agents, industrial dehydrating agents, sludge coagulants, thickening agents, condensation preventing agents for building materials, release control agents for chemicals and various other applications.

The present invention will be described in greater detail with reference to the drawing and the following examples.

DETAILED DESCRIPTION OF THE PREFERRED EMBODIMENT

Referring now to the drawing, there is illustrated a method and apparatus for the continuous manufacture of water absorbing resin, generally designated by reference numeral 10.

Generally, the apparatus 10 includes a plurality of monomer solution mixing vessels 12, 14, 16 and 18; an acrylic acid storage vessel 20, one or more neutralizing agent storage vessels such as potassium hydroxide storage vessel 22, sodium hydroxide storage vessel 24, ammonium hydroxide storage vessel 26, sodium carbonate storage vessel 28, potassium carbonate storage vessel 30 and neutralizing agent mixing vessels 32 and 34; one or more second monomer storage vessels, such as for acrylamide and styrene, 36 and 38; a plurality of thermal initiator storage vessels 40 and 42; a plurality of redox initiator storage vessels 44 and 46; an in-line mixer or blender 48 for blending the initiators with the mixed monomer solution; and a polymerization station, generally designated 50, including a pair of endless traveling conveyor belts 52 and 53, and a plurality of cross-linking agent storage vessels 54 and 56.

Acrylic acid solution from acrylic acid storage vessel 20, maintained at about 55-75° F. flows through valve 60 and pump 62 through insulated supply conduit 64 to a combining station 66 where the acrylic acid is combined with one or more neutralizing agents, such as potassium hydroxide from storage vessel 22, sodium hydroxide from storage vessel 24, and/or ammonium hydroxide from storage vessel 26 and may be combined with one or more other monomers such as acrylamide and/or styrene from second monomer storage vessels 36 and/or 38. The acrylic acid solution together with the aqueous solutions of one or more neutralizing agents and, optionally, one or more other monomers for copolymerization, are combined and fed through monomer solution feed conduits 68, 70, 72, 74, 76, and 78 to the four monomer solution mixing vessels 12, 14, 16 and 18. The monomer mixing vessels 12, 14, 16 and 18 are filled in a staggered time sequence such that one monomer mixing vessel, e.g., 12, is completely mixed and ready for transport to the inline blender 48 while the other monomer solution mixing vessels, e.g., 14, 16 and 18, are being filled such that after monomer mixing vessel 12 is depleted, one of the other monomer mixing vessels 14, 16 or 18 is sufficiently mixed and homogenized such that it is ready for transport of the mixed monomer solution to the blender 48 to maintain a continuous flow of mixed monomer solution to the blender 48 for continuous operation. In this manner, a continuous supply of mixed monomer solution is always ready for transport to the blender 48 to maintain the process continuously.

The potassium hydroxide solution stored in neutralizing agent storage vessel 22 is received, as supplied, at about a 45% by weight concentration as an aqueous solution and is pumped through pump 80 and conduits 82, 84, 86 and 88 to one or more potassium hydroxide storage vessels 32 and/or 34 where the potassium hydroxide solution can be further concentrated, for example to a preferred level of about 56% potassium hydroxide by weight, by the addition of a more concentrated form of potassium hydroxide, such as 100% solid potassium hydroxide, through hopper 90.

In accordance with the preferred apparatus, as shown in the drawing, either potassium hydroxide or ammonium carbonate can be added to the hopper 90 and the neutralizing agents conveyed through conduits 92, 94 and 96 to a vacuum separator 98 where the neutralizing agents are conveyed by diverter 100 to either a concentrated potassium hydroxide supply line 102 and concentrated potassium hydroxide storage vessel 106 or to a concentrated ammonium carbonate supply line 104 and concentrated ammonium carbonate storage vessel 108, respectively. The concentrated potassium hydroxide from vessel 106 is conveyed by a vibratory feeder 109 to diverter 110 where some of the concentrated potassium hydroxide, e.g., in solid form, is transported through conduit 112 to the potassium hydroxide tank 32 to increase the potassium hydroxide concentration to a desired level, e.g., 56% by weight potassium hydroxide. The diverter 110 conveys some of the potassium hydroxide through conduit 114 to a weigh hopper 116 such that some of the concentrated potassium hydroxide can be conveyed by vibratory feeder 118 to a turn head 120 for further, straight addition of potassium hydroxide to the monomer mixing vessels 12, 14, 16 and 18 through conduits 122, 124, 126 and 128.

The more concentrated aqueous solution of potassium hydroxide in vessel 32 is conveyed through conduits 132, 134 and 136 and pump 138 to the potassium hydroxide storage vessel 34 where the potassium hydroxide is stored at a suitable temperature, such as 65° F., through an internal heat transfer water supply line 140. The more concentrated potassium hydroxide from vessel 34 is fed to the mixing station 66 through an insulated supply conduit 142. Sodium carbonate from neutralizing agent supply vessel 28 can be supplied to the monomer solution mixing vessels 12, 14, 16 and/or 18 by vibratory feeder 144, conduit 146, weigh hopper 148, vibratory feeder 150 and turn head 152 through conduits 154, 156, 158 and 160. Sodium hydroxide can be conveyed directly from the sodium hydroxide storage vessel 24 through pump 159 and conduit 161 to the combining station 66. Optionally, the sodium carbonate can be substituted with or combined with potassium carbonate from neutralizing agent storage vessel 30, vibratory feeder 162 and conduit 164 leading to weigh hopper 148; or the sodium carbonate can be substituted for and/or combined with ammonium carbonate from ammonium carbonate vessel 108, vibratory feeder 166 and conduit 168 leading to weigh hopper 148, such that any desired neutralizing agent in any desired concentration can be fed directly to the monomer solution mixing vessels 12, 14, 16 and/or 18 through the conduits 154, 156, 158 and 160. Ammonium hydroxide from ammonium hydroxide storage vessel 26 optionally can be fed to the mixing station 66 and then to the monomer solution mixing vessels 12, 14, 16 and 18, as described, by feeding the ammonium hydroxide solution through pump 170 and conduits 172 and 174 to the mixing station 66, where the neutralizing agents are combined with the acrylic acid solution, and optionally, one or more other monomers from monomer storage vessel 36 or 38, monomer supply conduits 176 and 178, monomer weigh tank 180 and conduit 182 by pump 184. Optionally, additional monomer for copolymerization with acrylic acid can be supplied directly to the blender 48 for monomer storage vessel 38 through conduit 186, pump 188 and conduits 190 and 192. In this manner, any desired level of and combination of neutralizing agents and monomers can be supplied to the blender 48 for initiation and polymerization.

One or more cross-linking agents are stored in cross-linking agent storage vessels 54 and 56 where the cross-linking agent is weighed on scale 186 and fed manually, as indicated diagrammatically at 188, to the mixing station 66 for supply to the monomer solution mixing vessels 12, 14, 16 and 18.

In accordance with an important feature of the present invention, one or more thermal initiators are stored in the thermal initiator storage vessels 40 and 42 are delivered directly to the in-line blender 48 through conduits 190, 192 and 194 and pump 196 and, simultaneously, one or more redox initiators are supplied to the blender 48 through redox initiator storage vessel 44, conduit 200, pump 202 and conduits 204 and 206 for initiation of the mixed monomer solution. Optionally, some of the redox initiator from redox initiator storage tank 44 can be fed onto the surface of the mixed monomer solution as it travels on the liquid-impermeable endless conveyor belt 52 directing some of the initiator through conduit 208 directly onto the surface of the polymerizing mixed monomer solution, such as at spray head 210. Conveyor belt 53 is air-permeable to allow air to circulate over and through the polymerized and polymerizing acrylic acid and neutralized acrylic acid, as well as any other polymerized and polymerizing monomer delivered to the impermeable, first belt 52. The same or different redox initiator can be fed directly onto the surface of the polymerizing mixed monomer solution from initiator storage vessel 46 through conduit 212, pump 214 and conduits 216 and 218 through the spray head 210.

In accordance with another important feature of the present invention, a different, polymerization starting redox initiator is held in initiator storage vessel 46 which will initiate the mixed monomer solution at the temperature that the monomer solution has attained when it exits the in-line mixer 48, generally at the storage temperature of the mixed monomer solution in the monomer solution mixing vessels 12, 14, 6 and 18. Once the mixed monomer solution begins to polymerize as a result of the redox initiator from storage vessel 46, sufficient exothermic heat of reaction will maintain the polymerization reaction without further addition of the redox initiator from the initiator storage vessel 46. It has been found that sodium thiosulfate stored in redox initiator storage vessel 46 initiates the acrylic acid polymerization at a sufficiently low temperature that it can be used to start the polymerization reaction and, thereafter, is no longer needed once the polymerization has begun. Optionally, water can be supplied to the thermal initiator storage vessels 40 and 42 and to the redox initiator storage vessels 44 and 46 for diluting the initiator concentration from water supply line 220 and conduits 222, 224, 226, 228, 230, 232 and 234.

The polymerized dry (less than about 15% by weight water) polymer exits conveyor belt 53 through conduit 238 into a screw or auger discharge screw device 240 and is directed out of the discharge screw 240 through conduit 242 to a bucket elevator. The polymer then can be ground to any appropriate particle size distribution.

EXAMPLE 1

2,530 pounds of acrylic acid solution from acrylic acid storage vessel 20 at 110° F. and a concentration of 99% by weight flows through valve 60 and pump 62 through conduit 64 to a combining station 66 to vessel 12, 14, 16 or 18. Then 410 pounds of styrene from second monomer storage vessel 36 flows through pump 184 through conduits 176 and 178 to monomer weigh tank 180 and is charged to combining station 66 and then to vessel 12, 14 16 or 18, together with the acrylic acid.

1,700 pounds of a 45% by wt. potassium hydroxide is pumped from storage vessel 22, through pump 80, conduits 82, 84 86 and 88 to one or both potassium hydroxide storage vessels 32 and 34 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

650 pounds of potassium carbonate is supplied from vessel 28 to monomer solution mixing vessels 12, 14, 16 and/or 18 by vibratory feeder 144, through conduit 146, weigh hopper 148, vibratory feeder 150 and turn hed 152 through conduit 154, 156, 158 or 160.

2.9 pounds of N, N-methylenebisacrylamide crosslinking agent is weighed on scale 186 and fed manually as indicated diagrammatically at 188 to mixing station 66 for supply to the monomer solution mixing vessel 12, 14, 16 or 18, where the mixed monomer solution is agitated at 110° F.

The neutralized monomer from the monomer solution mixing vessel 12, 14, 16 or 18 is delivered to the impermeable first belt 52 through in-line mixer 48 where it is combined with a redox initiator and, a thermal initiator raising the temperature of the mixed monomer solution to 108° F., which is above the decomposition temperature of the thermal initiator. The thermal initiator is stored in thermal initiator storage vessels 40 and 42 consisting of a 12% solution of 2,2'-azobis-(2-amidinopropane) hydrochloric acid. 72.2 pounds of thermal initiator would be used for the above batch. The initiator is delivered to the in-line blender 48 through conduit 190, 192 and 194 and pump 199 and, simultaneously 24.1 pounds of 33% ammonium persulfate redox initiator is supplied to the blender 48 through redox initiator storage vessel 44, conduit 200, pump 202 and conduits 204 and 206 for the initiation of the mixed monomer solution.

3.0 pounds of a 33% by wt. solution of a 50/50 mixture of sodium thio sulfate and ammonia persulfate redox initiators stored in tank 44 is fed onto the surface of the polymerizing mixed monomer solution, such as a spray head 210.

EXAMPLE 2

2,940 pounds of acrylic acid solution from acrylic acid storage vessel 20 at 85° F. and a concentration of 99% by weight flows through valve 60 and pump 62 through conduit 64 to a combining station 66 to vessel 12, 14, 16 or 18.

1,700 pounds of a 45% by wt. potassium hydroxide solution is pumped from storage vessel 22, through pump 80, conduits 82, 84 and 88 to potassium hydroxide storage vessel 34 where the potassium hydroxide solution is stored. The potassium hydroxide solution is supplied from vessel 34 through conduit 142 and finally to vessel 12, 14, 16 or 18.

650 pounds of ammonium hydroxide is supplied from vessel 26 to monomer solution mixing vessels 12, 14, 16 and/or 18 by pump 170, through conduits 172 and 174.

2.9 pounds of N, N-methylenebisacrylamide crosslinking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The redox initiator raises the temperature of the mixed monomer solution to 150° F. The thermal initiator is stored in thermal initiator storage vessels 40 and 42 consisting of a 12% solution of 2,2'-azobis-(2-amidinopropane) hydrochloride. 72.2 pounds of thermal initiator would be used for the above batch. The initiator is delivered to the in-line blender 48 through conduit 190, 192 and 194 and pump 199 and, simultaneously 24.1 pounds of 33% ammonium sulfite redox initiator is supplied to the blender 48 through redox initiator storage vessel 44, conduit 200, pump 202 and conduits 204 and 206 for the initiation of the mixed monomer solution.

3.0 pounds of a 33% by wt. solution of a 50/50 mixture of sodium thio sulfate and ammonia persulfate redox initiators stored in tank 44 is fed onto the surface of the polymerizing mixed monomer solution, such as a spray head 210. After the monomer begins polymerization, the redox initiator is shut off at spray head 210.

EXAMPLE 3

2,600 pounds of acrylic acid solution from acrylic acid storage vessel 20 at 100° F. and a concentration of 99% by weight flows through valve 60 and pump 62 through conduit 64 to a combining station 66 to vessel 12, 14, 16 or 18.

1,600 pounds of a 45% by wt. potassium hydroxide solution is pumped from storage vessel 22, through pump 80, conduits 82, 84 and 88 to potassium hydroxide storage vessel 32 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

750 pounds of sodium hydroxide is supplied from vessel 24 to monomer solution mixing vessels 12, 14, 16 and/or 18 by pump 159, through conduit 161.

2.9 pounds of diethylenetriamine-diacrylamide crosslinking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The redox initiator raises the temperature of the mixed monomer solution to 150° F. The thermal initiator is stored in thermal initiator storage vessels 40 and 42 consisting of a 12% solution of azi-obisisobutyronitrile. 72.2 pounds of thermal initiator would be used for the above batch. The initiator is delivered to the in-line blender 48 through conduit 190, 192 and 194 and pump 199 and, simultaneously 24.1 pounds of 33% ammonium bisulfite persulfate redox initiator is supplied to the blender 48 through redox initiator storage vessel 44, conduit 200, pump 202 and conduits 204 and 206 for the initiation of the mixed monomer solution.

3.0 pounds of a 33% by wt. solution of a 50/50 mixture of sodium thio sulfate and ammonia persulfate redox initiators stored in tank 44 is fed onto the surface of the polymerizing mixed monomer solution, such as a spray head 210.

EXAMPLE 4

3,000 pounds of acrylic acid solution from acrylic acid storage vessel 20 at 110° F. and a concentration of 99% by weight flows through valve 60 and pump 62 through conduit 64 to a combining station 66 to vessel 12, 14, 16 or 18, where the mixed monomer solution is mixed at 110° F.

1,750 pounds of a 45% by wt. potassium hydroxide solution is pumped from storage vessel 22, through pump 80, conduits 82, 84 86 and 88 to one or both potassium hydroxide storage vessels 32 and 34 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

650 pounds of potassium carbonate is supplied from vessel 28 to monomer solution mixing vessels 12, 14, 16 and/or 18 by vibratory feeder 144, through conduit 146, weigh hopper 148, vibratory feeder 150 and turn hed 152 through conduit 154, 156, 158 or 160.

2.9 pounds of an ethylene glycol diallylester crosslinking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The redox initiator raises the temperature of the mixed monomer solution to 150° F. The thermal initiator is stored in thermal initiator storage vessels 40 and 42 consisting of a 10% solution of 4-t-butylazo-4'-cyanovaleric acid. 72.2 pounds of thermal initiator would be used for the above batch. The initiator is delivered to the in-line blender 48 through conduit 190, 192 and 194 and pump 199 and, simultaneously 24.1 pounds of 33% t-butylhydroproxide redox initiator is supplied to the blender 48 through redox initiator storage vessel 44, conduit 200, pump 202 and conduits 204 and 206 for the initiation of the mixed monomer solution.

3.0 pounds of a 33% by wt. solution of a 50/50 mixture of sodium thio sulfate and ammonia persulfate redox initiators stored in tank 44 is fed onto the surface of the polymerizing mixed monomer solution, such as a spray head 210.

EXAMPLE 5

2,500 pounds of acrylic acid solution from acrylic acid storage vessel 20 at 115° F. and a concentration of 99% by weight flows through valve 60 and pump 62 through conduit 64 to a combining station 66 to vessel 12, 14, 16 or 18. Then 400 pounds of styrene from second monomer storage vessel 36 flows through pump 184 through conduits 176 and 178 to monomer weigh tank 180 and is charged to combining station 66 and then to vessel 12, 14 16 or 18, together with the acrylic acid.

1,600 pounds of a 45% by wt. potassium hydroxide solution is pumped from storage vessel 22, through pump 80, conduits 82, 84 86 and 88 to one or both potassium hydroxide storage vessels 32 and 34 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

650 pounds of potassium carbonate is supplied from vessel 28 to monomer solution mixing vessels 12, 14, 16 and/or 18 by vibratory feeder 144, through conduit 146, weigh hopper 148, vibratory feeder 150 and turn hed 152 through conduit 154, 156, 158 or 160.

2.9 pounds of polyethylene glycol diacrylate crosslinking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The redox initiator raises the temperature of the mixed monomer solution to 150° F. The thermal initiator is stored in thermal initiator storage vessels 40 and 42 consisting of a 12% solution of 2,2'-azobis(2,4-dimethylvaleronitrile. 72.2 pounds of thermal initiator would be used for the above batch. The initiator is delivered to the in-line blender 48 through conduit 190, 192 and 194 and pump 199 and, simultaneously 24.1 pounds of 33% di-t-butyl hydroperoxide redox initiator is supplied to the blender 48 through redox initiator storage vessel 44, conduit 200, pump 202 and conduits 204 and 206 for the initiation of the mixed monomer solution.

3.0 pounds of a 33% by wt. solution of a 50/50 mixture of sodium thio sulfate and ammonia persulfate redox initiators stored in tank 44 is fed onto the surface of the polymerizing mixed monomer solution, such as a spray head 210.

EXAMPLE 6

2,530 pounds of acrylic acid solution from acrylic acid storage vessel 20 at 100° F. and a concentration of 99% by weight flows through valve 60 and pump 62 through conduit 64 to a combining station 66 to vessel 12, 14, 16 or 18. Then 410 pounds of styrene from second monomer storage vessel 36 flows through pump 184 through conduits 176 and 178 to monomer weigh tank 180 and is charged to combining station 66 and then to vessel 12, 14 16 or 18, together with the acrylic acid.

1,700 pounds of a 45% by wt. potassium hydroxide solution is pumped from storage vessel 22, through pump 80, conduits 82, 84 86 and 88 to one or both potassium hydroxide storage vessels 32 and 34 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

650 pounds of potassium carbonate is supplied from vessel 28 to monomer solution mixing vessels 12, 14, 16 and/or 18 by vibratory feeder 144, through conduit 146, weigh hopper 148, vibratory feeder 150 and turn hed 152 through conduit 154, 156, 158 or 160.

2.9 pounds of N, N-methylenebisacrylamide cross-linking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The redox initiator raises the temperature of the mixed monomer solution to 150° F. The thermal initiator is stored in thermal initiator storage vessels 40 and 42 consisting of a 12% solution of dimethyl 2,2'-azobisisobutyrate. 72.2 pounds of thermal initiator would be used for the above batch. The initiator is delivered to the in-line blender 48 through conduit 190, 192 and 194 and pump 199 and, simultaneously 24.1 pounds of 33% t-butylperbenzoate redox initiator is supplied to the blender 48 through redox initiator storage vessel 44, conduit 200, pump 202 and conduits 204 and 206 for the initiation of the mixed monomer solution.

EXAMPLE 7

2,530 pounds of acrylic acid solution from acrylic acid storage vessel 20 at 115° F. and a concentration of 99% by weight flows through valve 60 and pump 62 through conduit 64 to a combining station 66 to vessel 12, 14, 16 or 18. Then 410 pounds of acrylamide from second monomer storage vessel 38 flows through pump 188 through conduits 190 and 192 to the in-line mixer 48.

1,700 pounds of a 45% by wt. potassium hydroxide is pumped from storage vessel 22, through pump 80, conduits 82, 84 86 and 88 to one or both potassium hydroxide storage vessels 32 and 34 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

650 pounds of potassium carbonate is supplied from vessel 28 to monomer solution mixing vessels 12, 14, 16 and/or 18 by vibratory feeder 144, through conduit 146, weigh hopper 148, vibratory feeder 150 and turn hed 152 through conduit 154, 156, 158 or 160.

2.9 pounds of N, N-methylenebisacrylamide cross-linking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The thermal initiator raises the temperature of the mixed monomer solution to 150° F. The thermal initiator is stored in thermal initiator storage vessels 40 and 42 consisting of a 12% solution of 1,1'-azobis(l-cyclohexanecarbonitrile). 72.2 pounds of thermal initiator would be used for the above batch. The initiator is delivered to the in-line blender 48 through conduit 190, 192 and 194 and pump 199 and, simultaneously 24.1 pounds of 33% t-butylperoxyisopropylcarbonate redox initiator is supplied to the blender 48 through redox initiator storage vessel 44, conduit 200, pump 202 and conduits 204 and 206 for the initiation of the mixed monomer solution.

3.0 pounds of a 33% by wt. solution of a 50/50 mixture of sodium thio sulfate and ammonia persulfate redox initiators stored in tank 44 is fed onto the surface of the polymerizing mixed monomer solution, such as a spray head 210.

EXAMPLE 8

2,530 pounds of acrylic acid solution from acrylic acid storage vessel 20 at 115° F. and a concentration of 99% by weight flows through valve 60 and pump 62 through conduit 64 to a combining station 66 to vessel 12, 14, 16 or 18. Then 410 pounds of styrene from second monomer storage vessel 36 flows through pump 184 through conduits 176 and 178 to monomer weigh tank 180 and is charged to combining station 66 and then to vessel 12, 14 16 or 18, together with the acrylic acid.

1,700 pounds of a 45 % by wt. potassium hydroxide is pumped from storage vessel 22, through pump 80, conduits 82, 84 86 and 88 to one or both potassium hydroxide storage vessels 32 and 34 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

650 pounds of potassium carbonate is supplied from vessel 28 to monomer solution mixing vessels 12, 14, 16 and/or 18 by vibratory feeder 144, through conduit 146, weigh hopper 148, vibratory feeder 150 and turn hed 152 through conduit 154, 156, 158 or 160.

2.9 pounds of N, N-methylenebisacrylamide cross-linking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The redox initiator raises the temperature of the mixed monomer solution to 150° F. The thermal initiator is stored in thermal initiator storage vessels 40 and 42 consisting of a 10% solution of (1-phenylethyl)azodiphenylmethane. 72.2 pounds of thermal initiator would be used for the above batch. The initiator is delivered to the in-line blender 48 through conduit 190, 192 and 194 and pump 199 and, simultaneously 24.1 pounds of 33% peroxy-3,3,5-trimethylcyclohexane redox initiator is supplied to the blender 48 through redox initiator storage vessel 44, conduit 200, pump 202 and conduits 204 and 206 for the initiation of the mixed monomer solution.

3.0 pounds of a 33% by wt. solution of a sodium thio sulfate redox initiator stored in tank 44 is fed onto the surface of the polymerizing mixed monomer solution, such as a spray head 210.

EXAMPLE 9

2,530 pounds of acrylic acid solution from acrylic acid storage vessel 20 at 110° F. and a concentration of 99% by weight flows through valve 60 and pump 62 through conduit 64 to a combining station 66 to vessel 12, 14, 16 or 18. Then 410 pounds of styrene from second monomer storage vessel 36 flows through pump 184 through conduits 176 and 178 to monomer weigh tank 180 and is charged to combining station 66 and then to vessel 12, 14 16 or 18, together with the acrylic acid.

1,700 pounds of a 45% by wt. potassium hydroxide is pumped from storage vessel 22, through pump 80, conduits 82, 84 86 and 88 to one or both potassium hydroxide storage vessels 32 and 34 where the potassium hydroxide solution is further concentrated to a concentration of 53% by wt. and is pumped from vessel 32 through conduits 132, 134 and 136 and pump 138 to potassium hydroxide storage vessel 34 where the potassium hydroxide can be stored before transfer to mixing station 66 through the insulated supply conduit 142 and finally to vessel 12, 14, 16 or 18.

650 pounds of potassium carbonate is supplied from vessel 28 to monomer solution mixing vessels 12, 14, 16 and/or 18 by vibratory feeder 144, through conduit 146, weigh hopper 148, vibratory feeder 150 and turn hed 152 through conduit 154, 156, 158 or 160.

2.9 pounds of N, N-methylenebisacrylamide cross-linking agent is weighed on scale 186 and fed manually as indicated diagrammatically at 188 to mixing station 66 for supply to the monomer solution mixing vessel 12, 14, 16 or 18, where the mixed monomer solution is mixed at 110° F.

The neutralized monomer from the monomer solution mixing vessel 12, 14, 16 or 18 is delivered to the impermeable first belt 52 through in-line mixer 48 where it is combined with a thermal initiator and a redox initiator. The thermal initiator raises the temperature of the mixed monomer solution to 150° F. The thermal initiator is stored in thermal initiator storage vessels 40 and 42 consisting of a 12% solution of 2,2'-azobis-(2-methylbutyronitrile). 72.2 pounds of thermal initiator would be used for the above batch. The initiator is delivered to the in-line blender 48 through conduit 190, 192 and 194 and pump 199 and, simultaneously 24.1 pounds of 33% ammonium metabisulfite redox initiator is supplied to the blender 48 through redox initiator storage vessel 44, conduit 200, pump 202 and conduits 204 and 206 for the initiation of the mixed monomer solution.

3.0 pounds of a 33% by wt. solution of ammonia persulfate redox initiator stored in tank 44 is fed onto the surface of the polymerizing mixed monomer solution, such as a spray head 210.

What is claimed and sought to be secured by Letters Patent of the United States is:

1. A method of preparing a solid water absorbing resin comprising mixing a monomer solution of (A) acrylic acid neutralized 70-100 mole percent; and (B) a water-miscible to water-soluble polyvinyl monomer in a combined concentration of at least 30wt. %; with water to form a mixed monomer solution and initiating polymerization of monomers (A) and (B) by combining a thermal initiator and a redox initiator with the mixed monomer solution such that during polymerization, the exothermic heat of reaction is substantially the only heat energy used to accomplish polymerization, cross-linking and to drive off sufficient water to obtain a solid cross-linked resin having a water content of 15 percent by weight or less.

2. A process as defined in claim 1 wherein the continuous combined concentration of the liquid monomers (A) and (B) is at least 30 wt. % and less than 80 wt. %.

3. A process as defined in claim 1 wherein the mixed monomer solution has a temperature of 50 to 85° C. prior to polymerization.

4. A process as defined in claim 1 wherein monomer (B) is selected from the group consisting of N,N-methylenebisacrylamide and N,N-methylenebismethacrylamide.

5. A process as defined in claim 1 wherein the mixed monomer solution contains 1 to 10 wt. % of an organic solvent based on the weight of monomers (A) and (B).

6. A method of preparing a solid water absorbing resin comprising mixing a monomer solution of (A) acrylic acid neutralized 70-100 mole percent; and (B) a water-miscible to water-soluble polyvinyl monomer in a combined concentration of at least 30 wt. %; with water to form a mixed monomer solution, and adding a thermal initiator and a redox initiator to the mixed monomer solution to form an initiated mixed monomer solution, and wherein the mixed monomer solution is at a temperature below the decomposition temperature of the thermal initiator when the thermal initiator is added to the mixed monomer solution and wherein the temperature of the mixed monomer solution is high enough such that addition of the redox initiator thereto causes sufficient polymerization of the monomers to raise the temperature of the initiated mixed monomer solution to a level sufficient that the thermal initiator decomposes sufficiently to provide, together with the redox initiator, substantially complete polymerization.

7. The method of claim 6 wherein the thermal initiator and redox initiator substantially completely polymerize the mixed monomer solution such that less than about 1000 PPM free acrylic monomer remains in the polymerized resin.

8. The method of claim 7 wherein less than about 500 PPM free acrylic monomer remains in the polymerized resin.

9. The method of claim 7 wherein less than about 200 PPM free acrylic monomer remains in the polymerized resin.

10. The method of claim 5 further including the step of adjusting the temperature of the monomer mixture to a temperature of 30 to 85° C. prior to adding the initiators thereto.

11. The method of claim 10, further including the step of adjusting the temperature of the monomer mixture to a temperature of 35 to 75° C. prior to adding the initiator thereto.

12. The method of claim 10 further including the step of adjusting the temperature of the monomer mixture to a temperature of 45 to 55° C. prior to adding the initiators thereto.

13. A method of continuously reacting an acrylic acid monomer to produce a polyacrylate resin comprising:
mixing a monomer solution of (A) acrylic acid neutralized 70–100 mole percent; and (B) a watermiscible or water-soluble polyvinyl monomer in a combined concentration of at least 30 wt. %: with water to form a mixed monomer solution;
combining the mixed monomer solution with a thermal initiator and a redox initiator in a mixing chamber:
feeding the mixed monomer solution, thermal initiator and redox initiator to a polymerization station for polymerization;
polymerizing monomers (A) and (B) at the polymerization station while continuously feeding, simultaneously, the mixed monomer solution and the polymerization initiators for continuous polymerization; and
continuously removing solid polyacrylate resin from the polymerization station during polymerization.

14. The method of claim 13 wherein the polymerization station comprises an endless conveyor belt.

15. The method of claim 13 wherein the monomers of the mixed monomer solution consist essentially of (A) and (B).

16. The method of claim 13 wherein, during polymerization, the exothermic heat of reaction is substantially the only heat energy used to accomplish polymerization, cross-linking and to drive off sufficient water to obtain a solid cross-linked resin having a water content of 15 percent by weight or less.

17. The method of claim 13 wherein the continuous combined concentration of the liquid monomers (A) and (B) is at least 30 wt. % and less than 70 wt. %.

18. The method of claim 13 wherein the mixed monomer solution has a temperature of 50 to 75° C. prior to polymerization.

19. The method of claim 13 wherein monomer (B) is selected from the group consisting of N,N-methylenebisacrylamide and N,N-methylenebismethacrylamide.

20. The method of claim 13 further including the step of adjusting the temperature of the monomer mixture to a temperature of 40 to 85° C. prior to adding the initiators thereto.

21. The method of claim 13 including feeding the mixed monomer solution and the polymerization initiators to the mixing chamber at rates such that the combined concentration of polymerization initiators is present continuously in the mixed monomer solution in the mixing chamber in a concentration of at least 0.5 % by weight of monomers (A) and (B).

22. The method of claim 13 wherein the water content of said cross-linked resin is not greater than about 10 % by weight as recovered from the polymerized mixture, without an additional drying step.

23. The method of claim 13 including the step of pulverizing said cross-linked resin to form a powder.

24. The method of claim 13 including neutralizing the acrylic acid with an endothermically reacting neutralizing agent and an exothermically reacting neutralizing agent to control the temperature in the mixing chamber.

25. The method of claim 13 wherein the polyvinyl monomer (B) is maintained in the mixed monomer solution at a concentration of 0.2 to 0.6 wt. % based on the weight of monomers in the mixed monomer solution to produce a polyacrylate resin having a dry feel after substantial water absorption.

26. A method of preparing a solid water absorbing resin comprising mixing a monomer solution of (A) acrylic acid neutralized 70–100 mole percent; and (B) a water-miscible to water-soluble polyvinyl monomer in a combined concentration of at least 30 wt. %; with water to form a mixed monomer solution and initiating polymerization of monomers (A) and (B) by combining a thermal initiator and a redox initiator with the mixed monomer solution to accomplish polymerization and cross-linking to obtain a solid cross-linked resin.

27. A process as defined in claim 26 wherein the continuous combined concentration of the liquid monomers (A) and (B) is at least 30 wt. % and less than 80 wt. %.

28. A process as defined in claim 26 wherein the redox initiator comprises sodium thiosulfate.

29. A process as defined in claim 26 wherein monomer (B) is trimethylolpropane triacrylate.

* * * * *